United States Patent [19]

Hardman et al.

[11] 4,253,948

[45] Mar. 3, 1981

[54] DEHYDRATION OF WATER SOLUBLE MONOMERS WITH LIQUID CARBON DIOXIDE

[75] Inventors: Harley F. Hardman, Lyndhurst; Albert P. Schwerko, Solon, both of Ohio

[73] Assignee: Standard Oil Company, Cleveland, Ohio

[21] Appl. No.: 38,744

[22] Filed: May 14, 1979

[51] Int. Cl.³ .................... B01D 11/04; C07C 121/30; C07C 51/42

[52] U.S. Cl. .................... 210/634; 210/642; 260/465.9; 562/600; 203/DIG. 21

[58] Field of Search .................... 210/21, 59, 65; 260/705, 601 R, 465.9; 562/600; 560/218; 203/88, DIG. 21; 208/188, 321

[56] References Cited

U.S. PATENT DOCUMENTS

| | | | |
|---|---|---|---|
| 2,029,120 | 1/1936 | Schilling et al. | 55/65 |
| 2,744,855 | 5/1956 | Arnold | 208/188 |
| 2,922,815 | 1/1960 | Faerber | 203/62 |
| 3,133,018 | 5/1964 | Watanabe | 210/21 |
| 3,414,485 | 12/1968 | Speed | 203/DIG. 21 |
| 3,692,829 | 9/1972 | Sennewald et al. | 203/62 |
| 3,781,193 | 12/1973 | Sennewald et al. | 203/62 |

OTHER PUBLICATIONS

"Ternary Systems of Liquid Carbon Dioxide", Alfred W. Francis, *Journal of Physical Chemistry* 58, 1099 (1954).

*Primary Examiner*—Ivars C. Cintins
*Assistant Examiner*—E. Rollins Cross
*Attorney, Agent, or Firm*—David J. Untener; Herbert D. Knudsen; Larry W. Evans

[57] ABSTRACT

Separation of certain water soluble organic monomers such as acrylic acid from an aqueous solution can be accomplished by extraction with carbon dioxide, crystallizing the extract to remove carbon dioxide hydrate, and flashing off the remaining carbon dioxide solvent from the extract.

12 Claims, No Drawings

DEHYDRATION OF WATER SOLUBLE MONOMERS WITH LIQUID CARBON DIOXIDE

BACKGROUND OF THE INVENTION

It is well known in the art that carbon dioxide can be used for extraction of various petroleum fractions. Liquid carbon dioxide is advantageous because of its low cost, non-corrosiveness, non-toxicity and ease of recovery from the extract of raffinate phases. U.S. Pat. No. 2,029,120 discloses the separation of unsaturated hydrocarbons from gas mixtures using liquid carbon dioxide.

U.S. Pat. No. 2,631,966 shows the separation of various lubricating oils with carbon dioxide. As noted therein, liquid $CO_2$ has certain unusual miscibility relations with hydrocarbons. For example, it dissolves aliphatic and monocyclic aromatic hydrocarbons in preference to polycyclics of the same boiling range.

Typically, $CO_2$ has not been used alone, but as an aid to other solvents for extraction purposes. These solvents include liquid sulfur dioxide (U.S. Pat. No. 2,034,495) acetone (U.S. Pat. No. 2,246,227) and furfural or phenol (U.S. Pat. No. 2,281,865). A broad description of various solvents that can be used with carbon dioxide can be found in U.S. Pat. No. 2,631,966.

Liquid $CO_2$ has also been utilized to remove the solvents themselves from the extract phase, as can be found in U.S. Pat. No. 2,646,387.

The ability of $CO_2$ to function in the above systems will depend upon the solubility of $CO_2$ with other substances. "Ternary Systems of Liquid Carbon Dioxide" by Alfred W. Frances, *Journal of Physical Chemistry* 58, 1099 (1954) discloses the solubilities of 261 substances with carbon dioxide.

None of the processes above, however, disclose the ability or process for the dehydration of an aqueous solution by using $CO_2$.

There are a large number of processes for the production of certain organic chemicals that produce water as a by-product or use steam as a diluent during the reaction. Among these processes is the production of acrylic acid. The aqueous solution resulting from the reaction normally contains from 30–60% acrylic acid with the remainder being mostly water. Various methods have been proposed for removing this water, such as the addition of certain drying agents like calcium chloride as found in U.S. Pat. No. 2,922,815.

Other processes, such as for the production of acrylonitrile, use water as an aid in distilling acrylonitrile from the reactor effluent. This produces an aqueous solution of acrylonitrile that must be dehydrated.

The present invention provides a process for separating water from such aqueous solutions of organic chemicals that can achieve purities upwards of 99%.

DESCRIPTION OF THE INVENTION

The invention can be considered a process for the separation of water from an aqueous solution containing organic chemicals miscible with $CO_2$ by the steps of:

(a) contacting the aqueous solution with liquid carbon dioxide to form an extract phase of the organic chemical, carbon dioxide and some water, and a raffinate phase containing water;

(b) separating the extract phase from the raffinate phase;

(c) crystallizing by cooling and separating carbon dioxide hydrate from the extract phase; and (d) evaporating the carbon dioxide.

It is also possible to reverse steps c) and d) above such that the carbon dioxide solvent is partly evaporated prior to the crystallization and separation of the carbon dioxide hydrate.

The above process is especially suited for recovery of heat sensitive materials, such as acrylic acid, methacrylic acid, acrolein, methacrolein acrylonitrile or methacrylonitrile. However, it may be applied to any material having a favorable distribution coefficient between carbon dioxide and water. This distribution coefficient is the ratio of concentration of organics in carbon dioxide and water. If this ratio is greater than 1, than the co-efficient can be considered favorable.

A major advantage of the present invention is that operations are conducted at temperatures below 30° C., limiting thermal degradation or polymerization of the heat sensitive materials. This temperature limitation is because the critical temperature of carbon dioxide is 31.1° C.

The temperatures employed can vary depending on the step in the process. For example, one would not want to contact an aqueous solution containing acrylic acid at a temperature much below 10° C. Temperatures below this may cause crystals to form. However, during the crystallizing step, temperatures of about 0° C. can be used. The exact temperature will depend on factors such as the pressure used and the specific organic chemical to be dehydrated.

Since carbon dioxide is being utilized in a liquid state, pressures in the range of 370 to 1060 psig are required. The exact pressure will depend on the temperature, the specific organic chemical, the amount of organics being separated, and the $CO_2$/aqueous solution weight ratio. For example, in the separation of acrylic acid from water, pressures of from 450 to 850 psig are normally used.

The liquid $CO_2$ can be contacted with the aqueous solution either by batch operation or by continuous extraction. It is preferred to use continuous countercurrent extraction to perform the contacting and separation of the extract and raffinate phases. Such extraction processes are well known in the art.

Carbon dioxide hydrate is crystallized by cooling the extract phase to a temperature where the white crystals are formed and precipitate. For acrylic acid systems, this temperature is about 0° C.

After the crystals have been separated, which can be accomplished in a normal manner such as by filtration, the remaining carbon dioxide solvent is removed by simple reduction in pressure. This flashes off or evaporates the $CO_2$.

It is also possible to first evaporate part of the $CO_2$ and then cool the remaining solution to crystallize and separate the carbon dioxide hydrate. There should be about 0.31 g $CO_2$/gm of water remaining to form the hydrate. Some additional $CO_2$ should be present to prevent the product from crystallizing during the extraction.

The weight ratio of $CO_2$ to the aqueous solution will vary, dependent upon the amount of organics to be separated. Typically, this ratio is 2:1 but can be as low as 0.5:1 and high as 10 or 20:1. Preferred is the ratio between 1:1 and 3:1.

The carbon dioxide can be recovered, liquified and reused in the process.

EXAMPLE 1

A 31.2 wt. percent solution of acrylic acid in water was contacted with liquid $CO_2$ at about 25° C. and 840 psig. The weight ratio of $CO_2$: acrylic acid solution was 1.97. After equilibration, the lower aqueous phase was withdrawn, and the $CO_2$ phase was cooled to 0° C., where white crystals were formed. The crystals were separated from the liquid, and $CO_2$ evaporated from the liquid by gradual reduction of pressure. The remaining non-volatile liquid was found to be acrylic acid containing 0.9% water and a trace of dissolved $CO_2$.

EXAMPLE 2

A 34 wt. percent solution of acrylic acid in water was extracted with liquid $CO_2$ in a countercurrent extraction unit having six theoretical stages of contacting. Conditions were 25° C., 850 psig, solvent/feed (WT.)=3. Analysis of the extract and raffinate showed that 95.3% of the acrylic acid fed was recovered in the extract. The extract composition —after $CO_2$ removal—was 92.5% acrylic acid, 7.5% water. Cooling the extract to 0° C. and removing the crystals so formed yielded a product of composition 99% acrylic acid, 1% water (solvent free basis).

As can be seen above, extremely high purities of the organic chemicals can be achieved through the use of the present invention.

I claim:
1. In the process for the separation of water from an aqueous solution containing organic chemicals miscible with $CO_2$ by the steps of:
   (a) contacting the aqueous solution with liquid carbon dioxide to form an extract phase of the organic chemical, carbon dioxide and some water, and a raffinate phase containing water;
   (b) separating the extract phase from the raffinate phase;
   (c) crystallizing by cooling and separating carbon dioxide hydrate from the extract phase; and
   (d) evaporating the carbon dioxide.
2. The process of claim 1 wherein the contacting of step (a) occurs at a temperature below 31° C.
3. The process of claim 1 wherein the contacting of step (a) occurs at a pressure between 600 and 1050 psig.
4. The process of claim 2 wherein the carbon dioxide hydrate of step (c) is separated by filtration.
5. The process of claim 3 wherein $CO_2$ solvent is evaporated by reduction in pressure.
6. The process of claim 1 wherein the organic chemical is selected from the group of acrylic acid, methacrylic acid, acrolein, methacrolein, acrylonitrile or methacrylonitrile.
7. The process of claim 6 wherein the organic chemical is acrylic acid.
8. The process of claim 1 wherein the ratio of carbon dioxide to the aqueous solution is 1:1 to 3:1.
9. The process of claim 1 wherein the contacting of step (a) and the separation of step (b) occurs in an extraction column.
10. In the process for the separation of water from an aqueous solution containing organic chemicals miscible with $CO_2$ by the steps of:
   (a) contacting the aqueous solution with liquid carbon dioxide to form an extract phase of the organic chemical, carbon dioxide and some water, and a raffinate phase containing water;
   (b) separating the extract phase from the raffinate phase;
   (c) evaporating a part of the carbon dioxide from the extract phase;
   (d) crystallizing and separating carbon dioxide hydrate from the extract phase.
11. The process of claim 10 wherein the organic chemical is acrylic acid.
12. The process of claim 10 wherein contacting of step (a) occurs between a pressure of 600 and 1050 psig.

* * * * *